(12) United States Patent
Schachar

(10) Patent No.: US 7,780,727 B2
(45) Date of Patent: Aug. 24, 2010

(54) SCLERAL PROSTHESIS FOR TREATMENT OF PRESBYOPIA AND OTHER EYE DISORDERS

(75) Inventor: Ronald A. Schachar, Dallas, TX (US)

(73) Assignee: ReFocus Ocular, Inc., Dallas, TX (US)

( * ) Notice: Subject to any disclaimer, the term of this patent is extended or adjusted under 35 U.S.C. 154(b) by 0 days.

(21) Appl. No.: 09/940,722

(22) Filed: Aug. 27, 2001

(65) Prior Publication Data

US 2002/0026239 A1 Feb. 28, 2002

Related U.S. Application Data

(63) Continuation of application No. 09/061,168, filed on Apr. 16, 1998, now Pat. No. 6,280,468, which is a continuation-in-part of application No. 08/946,975, filed on Oct. 8, 1997, now Pat. No. 6,007,578.

(51) Int. Cl.
*A61F 2/14* (2006.01)
*A61F 9/013* (2006.01)
(52) U.S. Cl. .................................................. 623/4.1
(58) Field of Classification Search .................. 623/4.1, 623/6.64, 905, FOR. 103; 606/204.25; 604/FOR. 8
See application file for complete search history.

(56) References Cited

U.S. PATENT DOCUMENTS 3,064,643 A 11/1962 Dixon (Continued)

FOREIGN PATENT DOCUMENTS

FR 2 784 287 A1 4/2000
WO WO 99/17691 A1 4/1999

OTHER PUBLICATIONS

Ronald A. Schachar, MD, PhD, "Cause and Treatment of Presbyopia with a Method for Increasing the Amplitude of Accommodation", Annals of Ophthalmology, Dec. 1992, pp. 445-447, 452.

(Continued)

*Primary Examiner*—David H. Willse

(57) ABSTRACT

Presbyopia is treated by implanting within a plurality of elongated pockets formed in the tissue of the sclera of the eye transverse to a meridian of the eye, a prosthesis having an elongated body having a first surface and a second surface opposite the first surface to contact the base and flap of the scleral pocket. The first and second surfaces are spaced apart a distance so that the implanted prosthesis exerts an outward force on the flap of the scleral pocket which results in an outward traction on at least the anterior margin of the scleral pocket. The combined effect of the implanted prostheses is to exert a radially outward traction on the sclera in the region overlying the ciliary body which expands the sclera in the affected region together with the underlying ciliary body. The expansion of the ciliary body restores the effective working distance of the ciliary muscle in the presbyopic eye and thereby increases the amplitude of accommodation. Hyperopia, primary open angle glaucoma and/or ocular hypertension can be treated by increasing the effective working distance of the ciliary muscle according to the invention. A preferred embodiment of the scleral prosthesis has a major surface adapted to contact the base or flap of the pocket and an opposite surface or ridge spaced from the major surface.

55 Claims, 13 Drawing Sheets

U.S. PATENT DOCUMENTS

| | | | |
|---|---|---|---|
| 4,452,235 | A | 6/1984 | Reynolds |
| 4,521,210 | A * | 6/1985 | Wong .............................. 604/8 |
| 4,961,744 | A | 10/1990 | Kilmer et al. |
| 4,976,719 | A | 12/1990 | Siepser |
| 5,146,933 | A | 9/1992 | Boyd |
| 5,354,331 | A * | 10/1994 | Schachar .................... 623/4.1 |
| 5,558,630 | A | 9/1996 | Fisher |
| 5,766,242 | A | 6/1998 | Wong et al. |
| 5,824,086 | A | 10/1998 | Silvestrini |
| 6,299,640 | B1 * | 10/2001 | Schachar .................... 623/4.1 |

OTHER PUBLICATIONS

European Search Report dated Jul. 18, 2008 in connection with European Patent Application No. 06 00 7630.

Office Action dated Jun. 16, 2009 in connection with U.S. Appl. No. 09/972,533.

Office Action dated Aug. 12, 2009 in connection with U.S. Appl. No. 11/137,085.

Office Action dated Jan. 8, 2009 in connection with U.S. Appl. No. 09/972,533.

* cited by examiner

SCLERAL PROSTHESIS FOR TREATMENT OF PRESBYOPIA AND OTHER EYE DISORDERS

RELATIONSHIP TO OTHER APPLICATIONS

This application is a continuation of prior U.S. application Ser. No. 09/061,168 filed on Apr. 16, 1998, which issued as U.S. Pat. No. 6,280,468 on Aug. 28, 2001, which is a continuation-in-part of prior U.S. application Ser. No. 08/946,975 filed on Oct. 8, 1997, which issued as U.S. Pat. No. 6,007,578 on Dec. 28, 1999.

BACKGROUND OF THE INVENTION

1. Field of the Invention

This invention relates to methods of treating presbyopia, hyperopia, primary open angle glaucoma and ocular hypertension and more particularly to methods of treating these diseases by increasing the effective working distance of the ciliary muscle. The invention also relates to increasing the amplitude of accommodation of the eye by increasing the effective working range of the ciliary muscle.

2. Brief Description of the Prior Art

In order for the human eye to have clear vision of objects at different distances, the effective focal length of the eye must be adjusted to keep the image of the object focused as sharply as possible on the retina. This change in effective focal length is known as accommodation and is accomplished in the eye by varying the shape of the crystalline lens. Generally, in the unaccommodated emmetropic eye the curvature of the lens is such that distant objects are sharply imaged on the retina. In the unaccommodated eye near objects are not focused sharply on the retina because their images lie behind the retinal surface. In order to visualize a near object clearly, the curvature of the crystalline lens is increased, thereby increasing its refractive power and causing the image of the near object to fall on the retina.

The change in shape of the crystalline lens is accomplished by the action of certain muscles and structures within the eyeball or globe of the eye. The lens is located in the forward part of the eye, immediately behind the pupil. It has the shape of a classical biconvex optical lens, i.e., it has a generally circular cross section having two convex refracting surfaces, and is located generally on the optical axis of the eye, i.e., a straight line drawn from the center of the cornea to the macula in the retina at the posterior portion of the globe. In the unaccommodated human eye the curvature of the posterior surface of the lens, i.e., the surface adjacent to the vitreous body, is somewhat greater than that of the anterior surface. The lens is closely surrounded by a membranous capsule that serves as an intermediate structure in the support and actuation of the lens. The lens and its capsule are suspended on the optical axis behind the pupil by a circular assembly of very many radially directed elastic fibers, the zonules, which are attached at their inner ends to the lens capsule and at their outer ends to the ciliary muscle, a muscular ring of tissue, located just within the outer supporting structure of the eye, the sclera. The ciliary muscle is relaxed in the unaccommodated eye and therefore assumes its largest diameter. According to the classical theory of accommodation, originating with Helmholtz, the relatively large diameter of the ciliary muscle in this condition causes a tension on the zonules which in turn pulls radially outward on the lens capsule, causing the equatorial diameter of the lens to increase slightly and decreasing the anterior-posterior dimension of the lens at the optical axis. Thus, the tension on the lens capsule causes the lens to assume a flattened state wherein the curvature of the anterior surface, and to some extent the posterior surface, is less than it would be in the absence of the tension. In this state the refractive power of the lens is relatively low and the eye is focused for clear vision for distant objects.

When the eye is intended to be focused on a near object, the ciliary muscles contract. According to the classical theory, this contraction causes the ciliary muscle to move forward and inward, thereby relaxing the outward pull of the zonules on the equator of the lens capsule. This reduced zonular tension allows the elastic capsule of the lens to contract causing an increase in the antero-posterior diameter of the lens (i.e., the lens becomes more spherical) resulting in an increase in the optical power of the lens. Because of topographical differences in the thickness of the lens capsule, the central anterior radius of curvature decreases more than the central posterior radius of curvature. This is the accommodated condition of the eye wherein the image of near objects falls sharply on the retina.

Presbyopia is the universal decrease in the amplitude of accommodation that is typically observed in individuals over 40 years of age. In the person having normal vision, i.e., having emmetropic eyes, the ability to focus on near objects is gradually lost, and the individual comes to need glasses for tasks requiring near vision, such as reading.

According to the conventional view the amplitude of accommodation of the aging eye is decreased because of the loss of elasticity of the lens capsule and/or sclerosis of the lens with age. Consequently, even though the radial tension on the zonules is relaxed by contraction of the ciliary muscles, the lens does not assume a greater curvature. According to the conventional view, it is not possible by any treatment to restore the accommodative power to the presbyopic eye. The loss of elasticity of the lens and capsule is seen as irreversible, and the only solution to the problems presented by presbyopia is to use corrective lenses for close work, or bifocal lenses, if corrective lenses are also required for distant vision.

Certain rings and/or segments have been used in ocular surgery for various purposes. Rings and/or segments of flexible and/or elastic material, attached or prepared in situ by fastening the ends of strips of the material around the posterior portion of the globe, posterior to the pars plana (over the underlying retina), have been used to compress the sclera in certain posterior regions. Supporting rings of metal, adapted to fit the contour of the sclera have been used as temporary supporting structures during surgery on the globe. However, none of these known devices have been used for surgical treatment of presbyopia, and none have been adapted to the special needs of prosthetic devices used in treating presbyopia.

Accordingly, a need has continued to exist for a method of treating presbyopia that will increase the amplitude of accommodation of the presbyopic eye, thereby lessening or eliminating the need for auxiliary spectacle lenses to relieve the problems of presbyopia.

SUMMARY OF THE INVENTION

The treatment of presbyopia has now been facilitated by the prosthetic device of this invention which is implanted within a pocket formed within the tissue of the sclera of the globe of the eye in a zone of the sclera in the vicinity of the plane of the equator of the crystalline lens. The scleral pocket is formed by tunnelling through the tissue of the sclera in a circumferential direction in the defined zone of the globe. The scleral pocket thus has a base formed by the sclera tissue lying inward of the pocket, i.e., toward the interior of the globe, and a flap formed from the tissue located outward of the pocket. The scleral pocket accordingly resembles a belt loop. The prosthetic device of the invention comprises an elongated body having a first surface and a second surface opposite the first surface, the surfaces being adapted to contact the base and flap of the scleral pocket. The first and second surfaces are spaced apart a distance such that, when the prosthesis is implanted in the scleral pocket its opposed surfaces separate the base and flap of the scleral pocket thereby applying an outward force on the flap which results in an outward traction on at least the anterior margin of the scleral pocket. This traction elevates the portion of the sclera at the margin of the pocket and the ciliary body immediately beneath the sclera and attached thereto. This outward movement of the ciliary body increases the working distance of the ciliary muscle thereby allowing it to exert an increased force on the equator of the crystalline lens through the zonules. Preferably the prosthesis has an elongated planform and the first surface of the prosthesis is a major surface adapted to contact the base or flap of the scleral pocket. The second surface may be a relatively broad surface or a relatively narrow ridge extending along the planform of the prosthesis.

Accordingly, it is an object of the invention to provide a treatment for presbyopia.

A further object is to provide a treatment for presbyopia by increasing the effective working distance of the ciliary muscle in the presbyopic eye.

A further object is to provide a treatment for presbyopia by increasing the radial distance between the equator of the crystalline lens and the ciliary body.

A further object is to provide a treatment for presbyopia by implanting in the sclera a plurality of prostheses which will increase the working distance of the ciliary muscle.

A further object is to provide a prosthesis for implanting in the sclera of an eye that will increase the working distance of the ciliary muscle.

A further object is to provide a prosthesis for implanting in the sclera of an eye that will expand the sclera in the zone of the sclera surrounding the ciliary body.

A further object is to provide a prosthesis for implanting in the sclera of an eye that will increase the diameter of the ciliary body generally in the equatorial plane of the crystalline lens.

A further object is to provide a treatment for hyperopia.

A further object is to provide a treatment for primary open angle glaucoma.

A further object is to provide a treatment for ocular hypertension.

A further object is to provide a treatment for increasing the amplitude of accommodation of the eye.

Further objects of the invention will become apparent from the description of the invention which follows.

DETAILED DESCRIPTION OF THE INVENTION AND PREFERRED EMBODIMENTS

Figure 1:
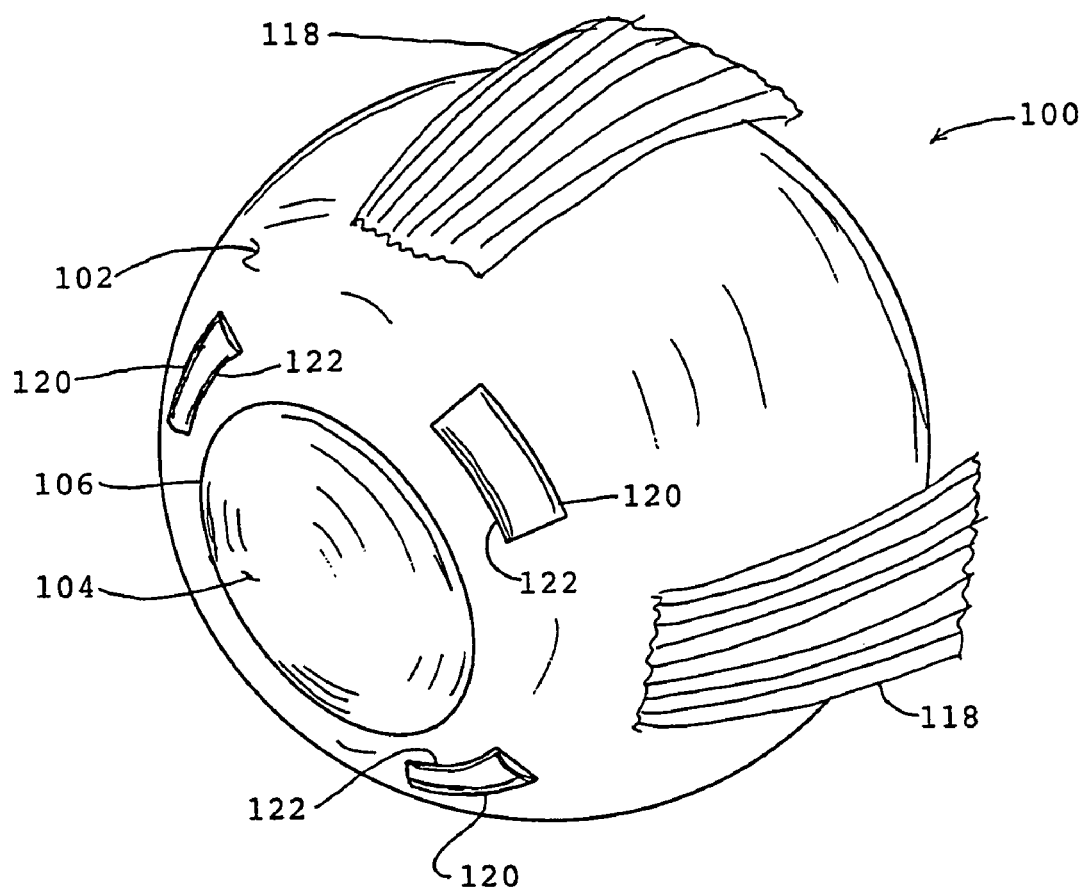
FIG. 1 shows an isometric view of an eye having the prosthesis of this invention implanted therein.

This invention is based on a different theory, developed by the inventor, which has been described in U.S. Pat. No. 5,354, 331, the entire disclosure of which is incorporated herein by reference, regarding the cause of the loss of amplitude of accommodation that constitutes presbyopia. According to the invention, presbyopia is treated by increasing the effective working distance of the ciliary muscle. This is accomplished by increasing the distance between the ciliary muscle and the lens equator by increasing the diameter of the sclera in the region of the ciliary body.

According to the invention the effective working distance of the ciliary muscle is increased by implanting in pockets surgically formed in the sclera of the eye a plurality of prostheses designed to place an outward traction on the sclera in the region of the ciliary body. The relevant anatomy of the eye for locating the scleral pockets may be seen by reference to FIGS. 1-4. The outermost layer of the eye 100 comprises the white, tough sclera 102 which encompasses most of the globe and the transparent cornea 104, which constitutes the anterior segment of the outer coat. The circular junction of the cornea and sclera is the limbus 106. Within the globe of the eye, as illustrated in the cross-section of FIG. 4, the crystalline lens 108 is enclosed in a thin membranous capsule and is located immediately posterior to the iris 112, suspended centrally posterior to the pupil 114 on the optical axis of the eye. The lens 108 is suspended by zonules extending between the lens capsule at the equator 110 of the lens 108 and the ciliary body 116. The ciliary body 116 lies just under the sclera 102 (i.e., just inwardly of the sclera 102) and is attached to the inner surface of the sclera 102. As may be seen in FIG. 4, the ciliary body 116 lies generally in a plane 130 defined by the equator 110 of the lens 108. The plane 130 can also be extended to intersect the sclera 102 whereby it forms a generally circular intersection located about 2 millimeters posterior to the limbus 106. The external muscles 118 of the eyeball control the movement of the eye.

According to the invention a generally outwardly directed traction is exerted on the sclera in the region of the ciliary body to expand the sclera 102 in that region. This expansion of the sclera 102 produces a corresponding expansion of the attached ciliary body 116 and moves the ciliary body 116 outwardly away from the equator of the lens 108, generally in the plane 130 of the equator 110 of the lens 108. The sclera 102 is preferably expanded approximately in the plane of the equator of the lens 108. However, any expansion of the sclera 102 in the region of the ciliary body 116, i.e., in the region of the sclera somewhat anterior or posterior to the plane of the equator 110 of the lens 108 is within the scope of the invention, provided that such expansion of the sclera 102 moves the ciliary body 116 away from the equator 110 of the lens 108. Typically, the expansion of the sclera will be accomplished in the region from about 1.5 millimeters anterior to the plane 130 of the equator of the lens 108 to about 2.5 millimeters posterior to that plane, i.e., from about 0.5 millimeters to about 4.5 millimeters posterior to the limbus 106. Accordingly, the anterior margin 122 of a scleral pocket 120 will be located in that region of the sclera.

The prosthesis of the invention is designed to apply an outwardly directed traction to the sclera at the general position of the anterior margin 122 of a scleral pocket 120. Accordingly, the prosthesis has an elongated body with a first surface and a second surface each adapted to contact the base of the scleral pocket or the flap of the scleral pocket. The surfaces are spaced apart by the body of the prosthesis by a distance sufficient to cause the flap to exert an outward traction on at least the anterior margin of the scleral pocket, with the effect on the adjacent sclera and ciliary body as discussed above.

Although the surfaces can have any suitable shape that accomplishes the purpose of the prosthesis, it is generally preferred that the prosthesis have a base having one major surface adapted to contact a major portion of the base or flap of the scleral pocket. The base typically has an elongated planform and is oriented generally circumferentially with respect to the circle defined on the sclera by the intersection therewith of the plane 130 of the equator 110 of the lens 108.

The second, opposite, surface of the scleral prosthesis may be relatively broad in an antero-posterior dimension, or it may have a relatively narrow ridge extending along at least a substantial portion of the elongated planform. The prosthesis may be implanted within the scleral pocket or may extend beyond at least one end of the scleral pocket. It is preferable that the prosthesis be of a sufficient length to extend beyond the ends of the scleral pocket and contact the outer surface of the intact sclera.

Figure 4:
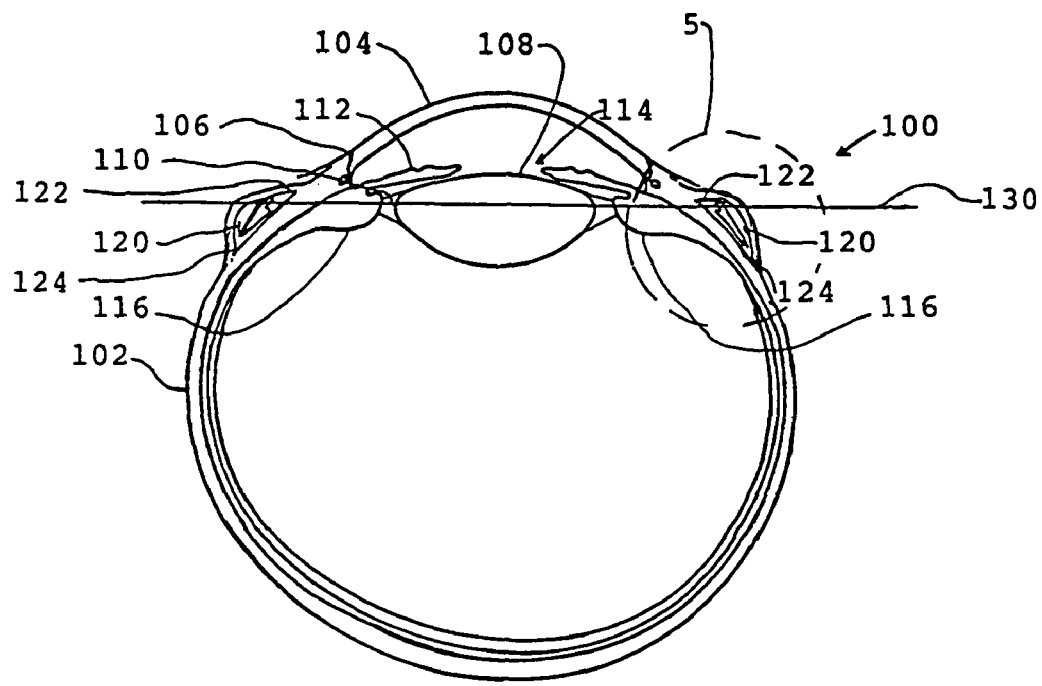
FIG. 4 shows a cross section of the eye of FIG. 2 along the line 4-4.
Figure 5:
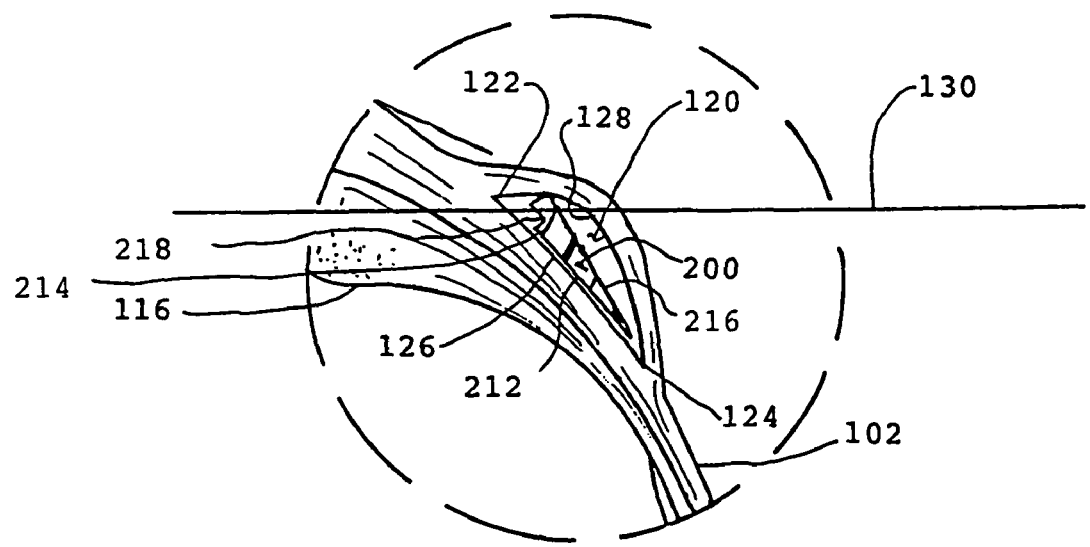
FIG. 5 shows an enlarged view of the cross section of FIG. 4 in the region indicated by the circle 5.
Figure 6:
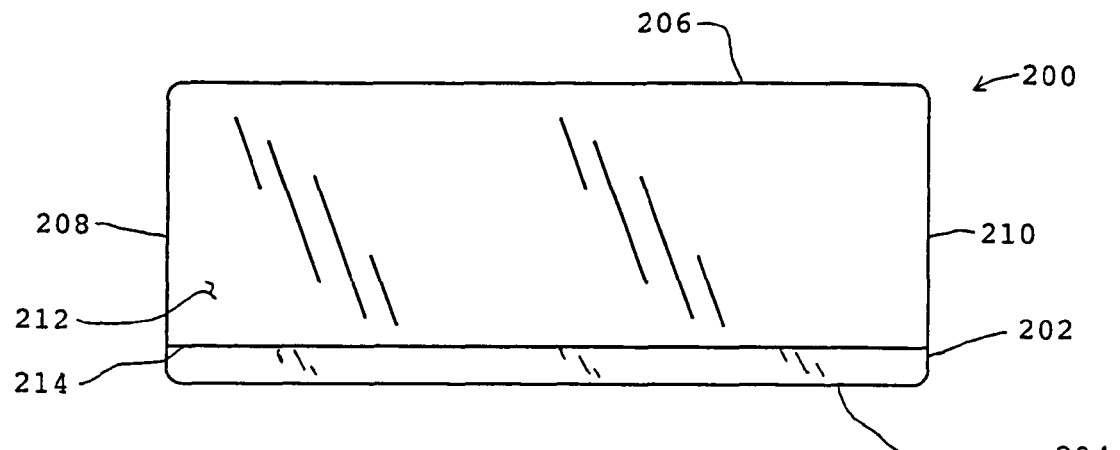
FIG. 6 shows a plan view of a rectangular embodiment of the prosthesis of the invention having a flat base.
Figure 7:
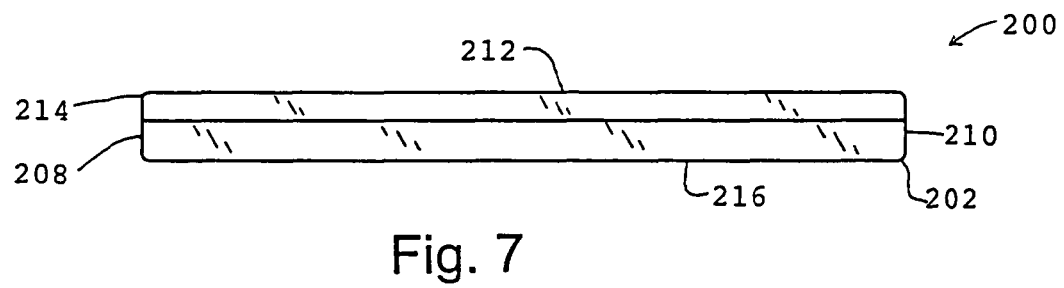
FIG. 7 shows a front elevational view of the prosthesis illustrated in FIG. 6.
Figure 8:
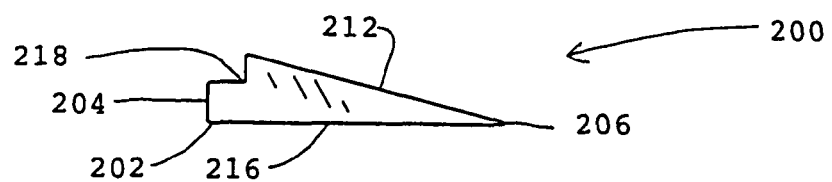
FIG. 8 shows an end elevational view of the prosthesis shown in FIG. 6.

The position of one embodiment of the prosthesis within a scleral pocket and its operation to expand the sclera are illustrated in FIGS. 4 and 5, showing a prosthesis of the type illustrated in FIGS. 6-8.

The base member 202 of the prosthesis 200 has a smooth exterior face 216 adapted to be placed in contact with the internal surface of the outer wall 128 of the scleral pocket 120. The opposite, or interior, face 212 of the prosthesis 200 is provided with a ridge 214 extending along a substantial portion of the length of the base 202. This ridge bears against the inner wall 126 of the scleral pocket 120. Accordingly, the sclera 102 at the anterior margin 122 of the scleral pocket 120 is elevated above its original level. The attached ciliary body 116 is thereby also expanded away from the equator 110 of the lens 108, and the working distance of the ciliary muscle is increased.

A first embodiment of the prosthesis of the invention is illustrated in FIGS. 6-8. FIG. 6 shows a plan view of the inner face of the prosthesis 200 having a base 202 with an anterior edge 204, a posterior edge 206, and lateral ends 208 and 210. The inner face 212 is provided with a ridge 214 extending along the length of the major dimension of the elongated base 202. FIG. 7 shows a front elevational view of the prosthesis of FIG. 6 showing the flat, smooth outer surface 216 of the prosthesis. FIG. 8 shows a side view of the prosthesis showing the outer surface 216, the ridge 214 and a notch 218 on the inner surface 212 of the prosthesis.

Figure 3:
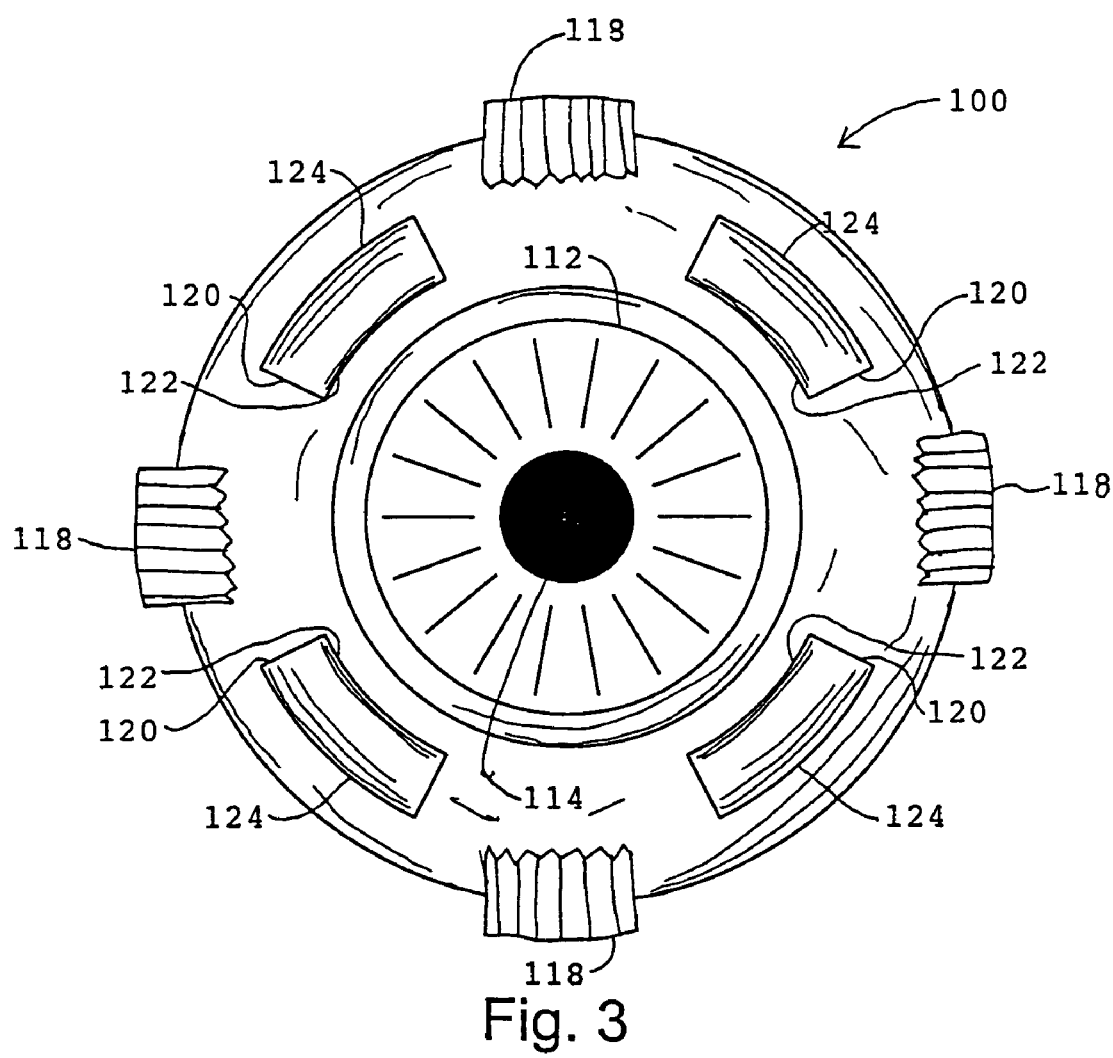
FIG. 3 shows a front elevational view of an eye showing the location of straight scleral pockets.
Figure 9:
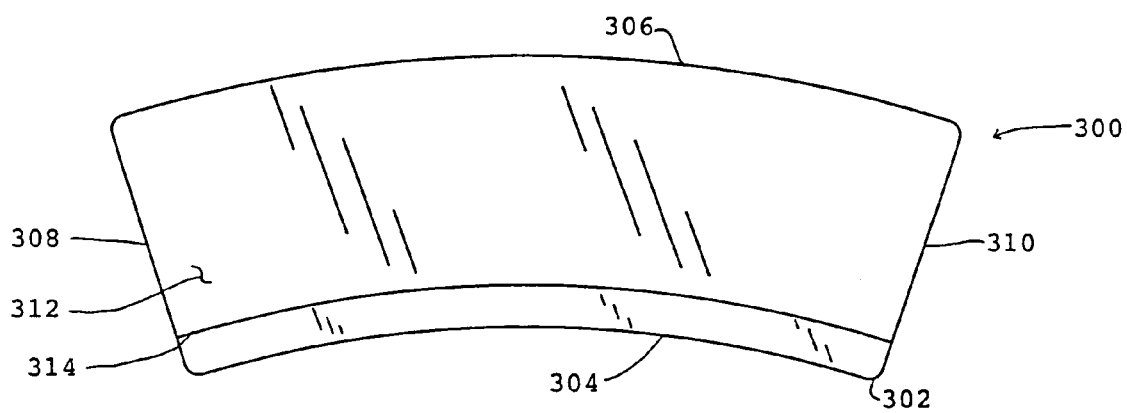
FIG. 9 shows a plan view of an embodiment of the prosthesis that is curved in the plane of the base.
Figure 10:
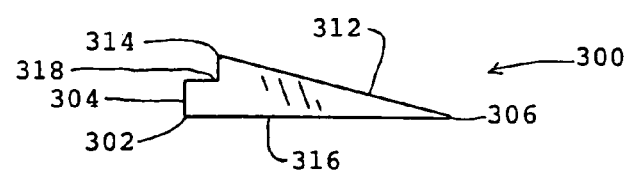
FIG. 10 shows an end view of the prosthesis of FIG. 9.

FIGS. 9-10 illustrate a prosthesis of the invention having a curved planform adapted to be implanted in a scleral pocket that is curved to match the curvature of the eyeball. The prosthesis 300 of FIGS. 9-10 has a generally planar base 302, curved in the plane of the base 302, having an anterior edge 304, a posterior edge 306, and lateral ends 308 and 310. The inner face is provided with a ridge 314 extending along the length of the major dimension of the elongated curved base 302. FIG. 10 shows an end view of the prosthesis of FIG. 9 showing the outer face 316, the ridge 314 and a notch 318 on the inner face 312 of the prosthesis. The curvature of the base is chosen to provide at least an approximate match for the curvature of the adjacent structures on the surface of the sclera, e.g., the limbus 106, adjusted for the distance of the scleral pocket 120 and prosthesis 300 from the limbus 106. FIG. 3 shows a front elevational view of an eye provided with curved scleral pockets 120 to accommodate a curved prosthesis 300 of the type illustrated in FIGS. 9 and 10.

Figure 11:
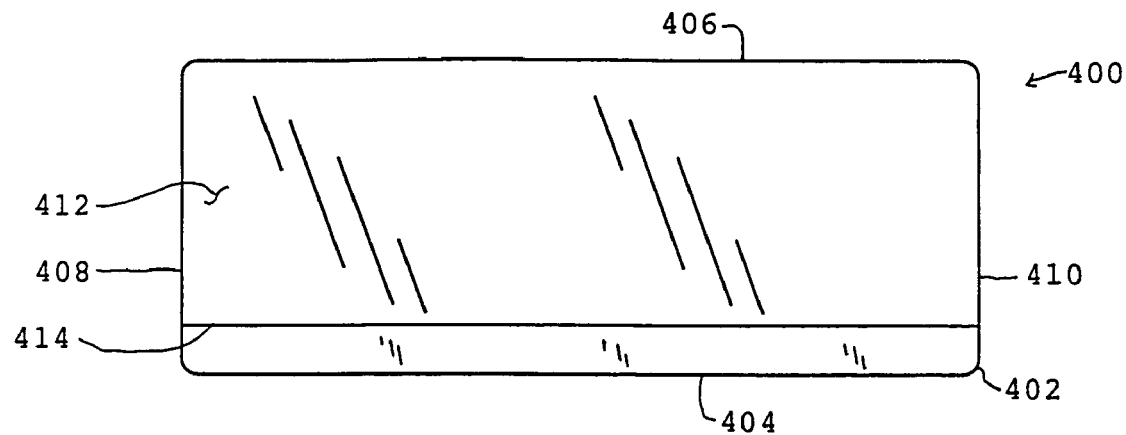
FIG. 11 illustrates a plan view of an alternate embodiment of the prosthesis of the invention.
Figure 12:
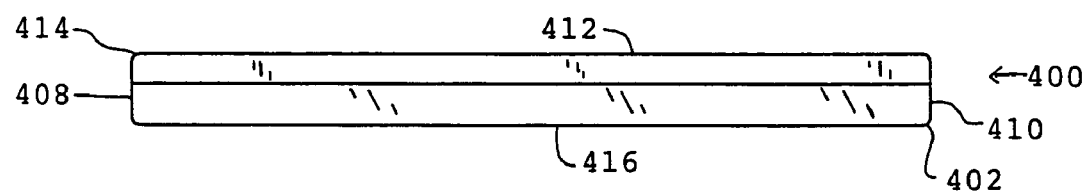
FIG. 12 shows a front elevational view of the prosthesis illustrated in FIG. 11.
Figure 13:
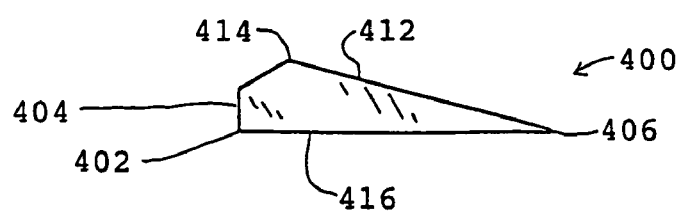
FIG. 13 shows an end elevational view of the prosthesis of FIG. 11.

FIGS. 11-13 show an embodiment of the invention wherein the anterior portion is tapered from the ridge to the anterior edge. FIG. 11 shows a plan view of the prosthesis 400 having a base 402 with an anterior edge 404, a posterior edge 406, and lateral ends 408 and 410. The outer face 416 is smooth and adapted to be placed against the inner surface of the outer wall 128 of a scleral pocket 120. The inner face 412 is provided with a ridge 414 extending along the length of the major dimension of the elongated base 402. FIG. 12 shows a front elevational view of the prosthesis of FIG. 11 showing the flat, smooth outer face 416 of the prosthesis. FIG. 13 shows an end view of the prosthesis of FIG. 11 showing the outer face 416 and the ridge 414 on the inner face 412 of the prosthesis 400. In this embodiment the ridge 414 tapers toward the anterior edge 404 of the prosthesis.

Figure 14:
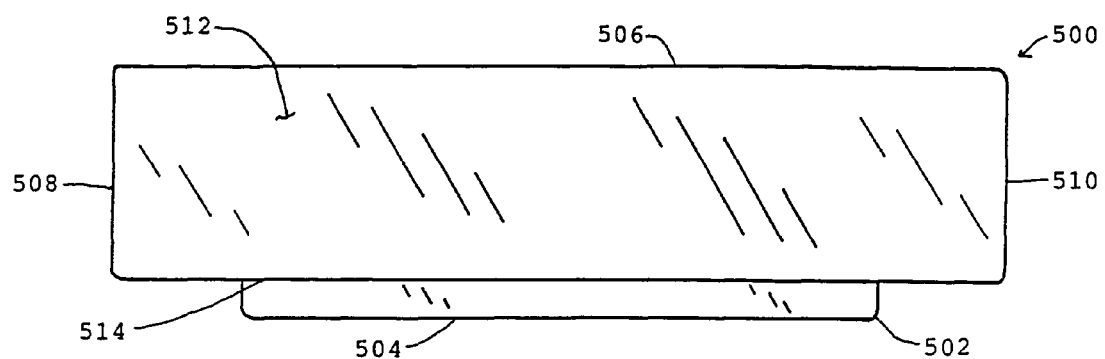
FIG. 14 illustrates a plan view of an embodiment of the invention in which the ridge member extends beyond the end of the base member.
Figure 15:
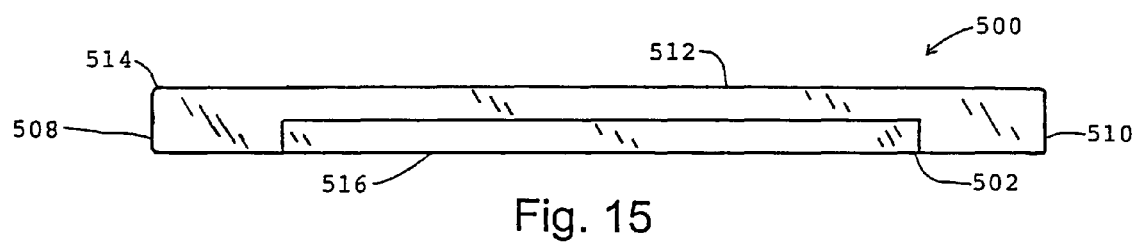
FIG. 15 shows a front elevational view of the prosthesis illustrated in FIG. 14.
Figure 16A:
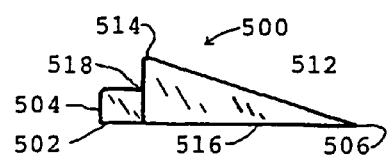
FIG. 16a shows an end elevational view of the prosthesis of FIG. 14, wherein the base prosthesis is tapered to the posterior edge.
Figure 16B:
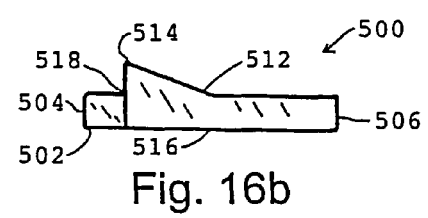
FIG. 16b shows an end elevational view of a prosthesis similar to that shown in FIGS. 14, 15 and 16a, wherein the base is not tapered.

FIGS. 14-16 show a preferred embodiment of the prosthesis in which the ridge member includes extensions beyond the ends of the base member which lie on the surface of the sclera adjacent to the scleral pocket and help to stabilize the prosthesis. FIG. 14 shows a plan view of this embodiment 500 having a base 502 with an anterior edge 504, a posterior edge 506, and lateral ends 508 and 510. The inner face 512 is provided with a ridge 514. The ends 508 and 510 of the ridge 514 extend slightly beyond the ends of the base 502. Accordingly, the ends 508 and 510 of the ridge 514 will extend beyond the ends of the pocket 120 and lie on the surface of the sclera 102. FIG. 15 shows a front elevational view of the prosthesis of FIG. 14 showing the flat, smooth outer face 516 of the prosthesis and the ends 508 and 510 of the ridge 514 extending beyond the ends of the base 502. FIG. 16a shows an end view of the prosthesis of FIG. 14 showing the smooth outer face 516 and the ridge 514 on the inner face 512 of the base 502, as well as a notch 518. FIG. 16b shows an end view of an alternate embodiment of the prosthesis 500 wherein the base 502 does not taper all the way to the posterior edge 506. Evidently, the thickness of the posterior edge 506 may vary from a relatively sharp posterior edge as shown in FIG. 16a to a relatively thick posterior edge as shown in FIG. 16b, or even thicker if it is advantageous.

Figure 17:
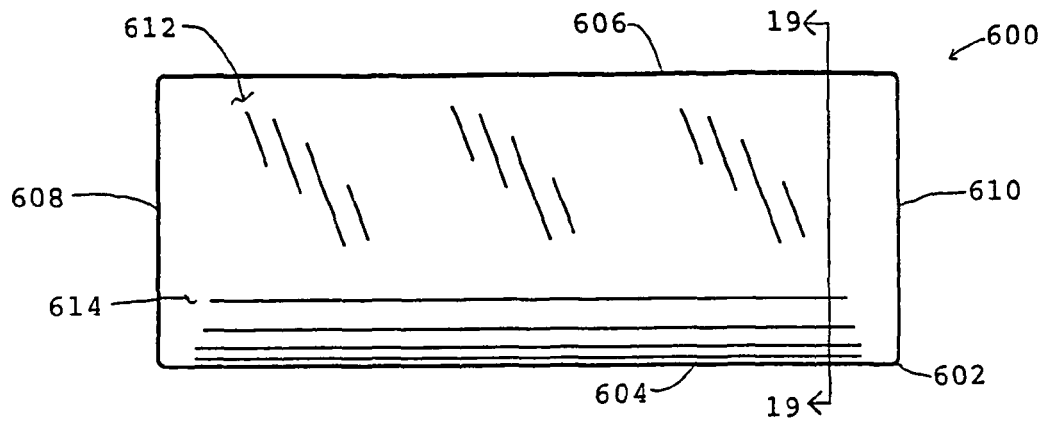
FIG. 17 shows a plan view of an embodiment of the prosthesis of the invention wherein the prosthesis is hollow and made of an elastomeric material that is filled with a liquid.
Figure 18:
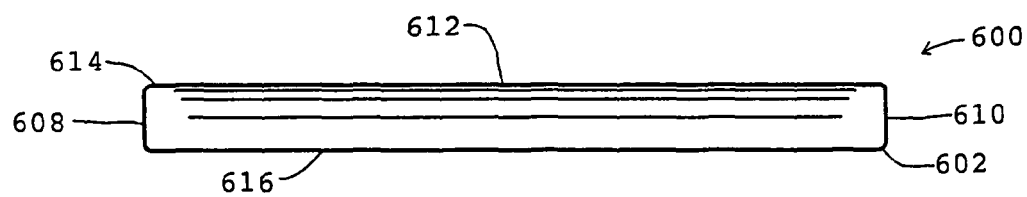
FIG. 18 shows a front elevational view of the prosthesis illustrated in FIG. 17.
Figure 19:
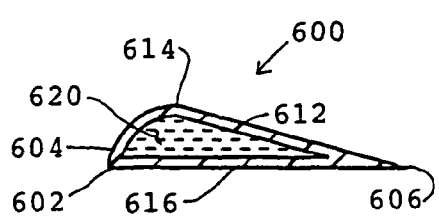
FIG. 19 shows a cross sectional view of the prosthesis of FIG. 17 along the line 19-19.
Figure 20:
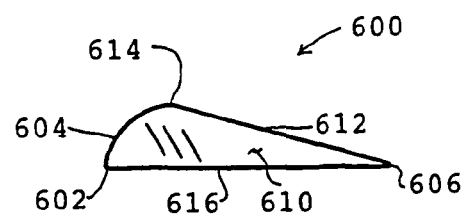
FIG. 20 shows an end elevational view of the prosthesis of FIG. 17.

FIGS. 17-20 illustrate an embodiment of the prosthesis that is hollow and made from a plastic or elastomeric material and filled with a liquid. FIG. 17 shows a plan view of this embodiment 600 having a base 602 with an anterior edge 604, a posterior edge 606, and lateral ends 608 and 610. The inner face 612 is smoothly rounded and rises to a crest 614 that serves to support the prosthesis on the inner wall 126 of the scleral pocket 120 in the same way as the ridge member of other embodiments of the invention. FIG. 18 shows a front elevational view of the prosthesis of FIG. 17 showing the flat, smooth outer face 616 of the prosthesis. FIG. 19 shows a cross section of the prosthesis of FIG. 17 taken along the line 19-19. The cross-section shows the flexible wall 612 of the prosthesis as well as the flat outer face 616, and the crest 614. The cross section also shows the filling liquid 620. FIG. 20 shows an end view of the prosthesis of FIG. 17 showing the outer face 616 and the crest or ridge 614 on the inner face 612 of the prosthesis 600. The hollow prosthesis is filled with liquid, typically by injecting the liquid through an end 608 or 610. The prosthesis may be filled with more or less liquid in order to adjust the thickness between the outer face 616 and the crest or ridge 614 to provide more or less traction on the sclera at the anterior margin 122 of the scleral pocket or belt loop 120.

Figure 21:
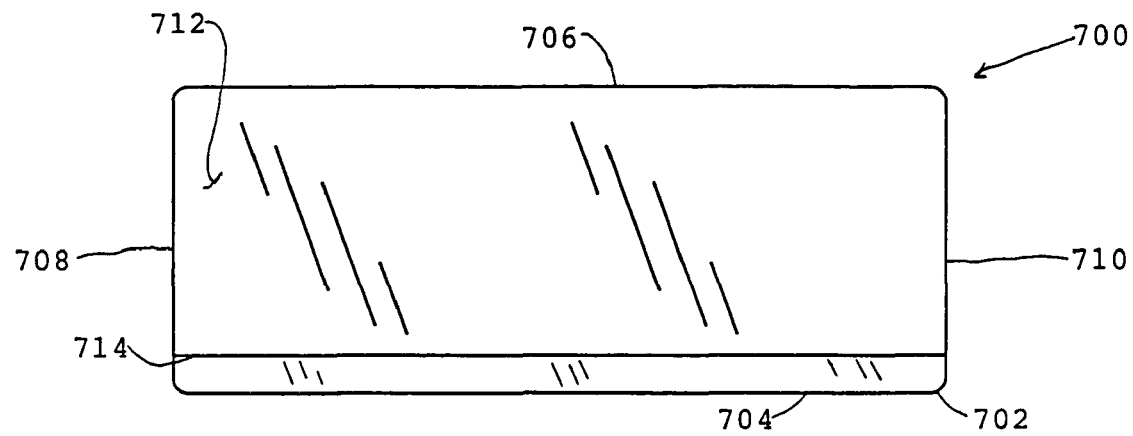
FIG. 21 illustrates a plan view of an embodiment of the prosthesis of the invention wherein the base is curved to match the curvature of the globe.
Figure 22:
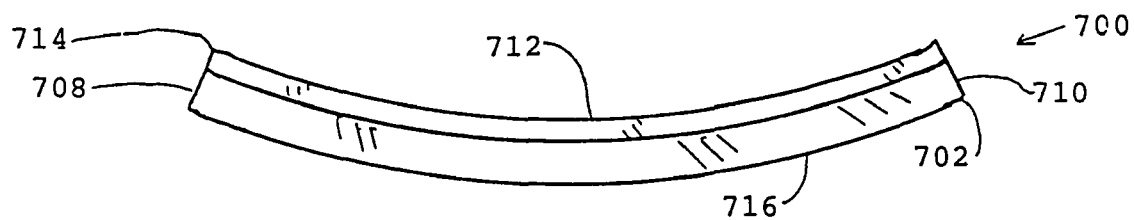
FIG. 22 shows a front elevational view of the prosthesis illustrated in FIG. 21.
Figure 23:
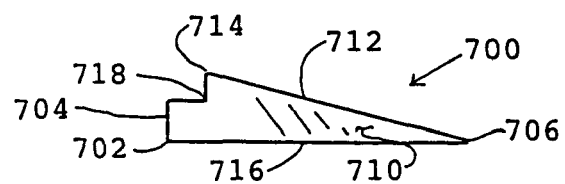
FIG. 23 shows an end elevational view of the prosthesis of FIG. 21.
Figure 24:
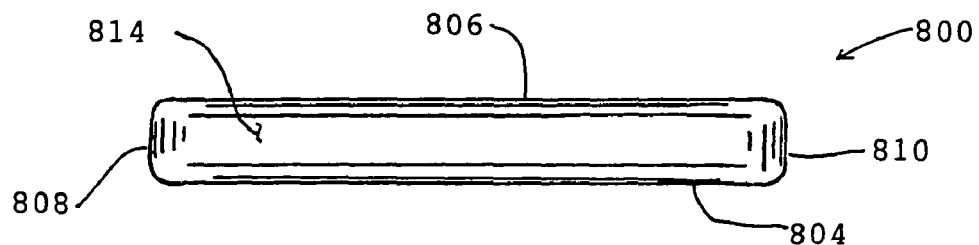
FIG. 24 illustrates a plan view of an alternate embodiment of the prosthesis of the invention having a curved surface adapted to contact the base of the scleral pocket.
Figure 25:
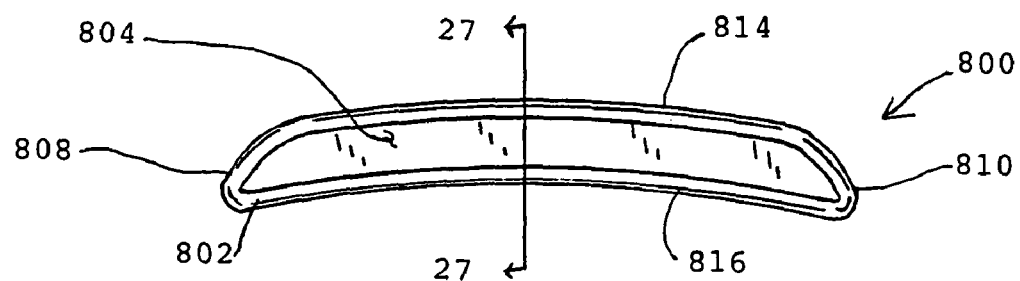
FIG. 25 shows a front elevational view of the prosthesis illustrated in FIG. 24.
Figure 26:
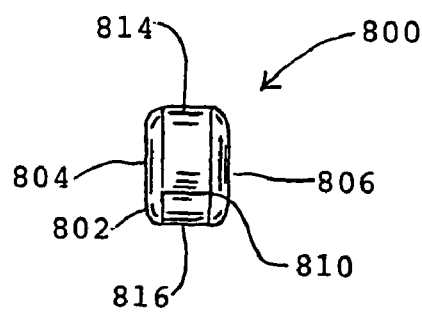
FIG. 26 shows an end elevational view of the prosthesis of FIG. 24.
Figure 27:
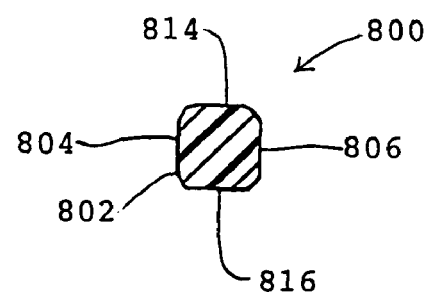
FIG. 27 shows a cross-section of the prosthesis shown in FIG. 24 along the line 27-27.

FIGS. 21-23 illustrate an embodiment of the invention generally similar to that shown in FIGS. 6-8, having, however, a base in which the inner face of the prosthesis is curved to provide an approximate match to the curvature of the globe. FIG. 21 shows a plan view of the inner face of the prosthesis 700 having a base 702 with an anterior edge 704, a posterior edge 706, and lateral ends 708 and 710. The inner face 712 is provided with a ridge 714 extending along the length of the major dimension of the elongated base 202. FIG. 22 shows a front elevational view of the prosthesis of FIG. 21 showing the curved, smooth outer surface 716 of the prosthesis. FIG. 23 shows an end view of the prosthesis showing the outer surface 716, the ridge 714 and a notch 718 on the curved inner surface 712 of the prosthesis.

A preferred embodiment of the scleral prosthesis is that shown in FIGS. 9 and 10, wherein the anterior rim 304 and the posterior rim 306 are both generally circular arcs. The taper in the diameter of the segment is preferably selected in an individual case to fit the globe in the region of the ciliary body. Accordingly, different sizes of segments will be provided wherein the radius of curvature of the anterior rim ranges from about 7.0 to about 10 millimeters in 0.50 millimeter increments. Accordingly, a preferred segment has a typical internal circular radius of curvature at its anterior portion of about 7.76 millimeters, at the position of the ridge of about 8.21 millimeters, and at the posterior rim of about 8.91 millimeters. The preferred segment has outer radius of curvature at its anterior portion of 8.02 millimeters, at its mid portion 8.47 millimeters, and at its base 8.94 millimeters. These measurements will vary depending on the size of the eye, the amount of rigidity required, and the strength of the material from which the segment is made. The preferred anterior chord length of the segment is 5 millimeters. The axial width of the segment will typically be about 2 millimeters.

FIGS. 24-27 illustrate another preferred embodiment 800 of the scleral prosthesis of the invention having a curved surface to contact the base 126 of the scleral pocket and an elevated ridge or opposite surface to contact the inner side 128 of the flap of the scleral pocket 120. This embodiment 800 has a base 802 having a smooth surface 816. The prosthesis 800 has an anterior edge 804 and posterior edge 806, which are relatively flat surfaces as shown. Opposite the base surface 816 is an elevated surface or ridge 814. In the illustrated embodiment the elevated surface or ridge 814 is relatively broad in an antero-posterior, or axial, dimension. However, the ridge 814 may be relatively narrower or broader than shown. The prosthesis 800 has lateral ends 808 and 810. The prosthesis 800 is shown as having a curved base surface 816. The surface 816 may also be flat or straight in the transverse dimension. However it is preferred that the surface 816 be curved as shown to generally match the curvature of the sclera in the zone adjacent to and contiguous with the ciliary body.

Figure 28:
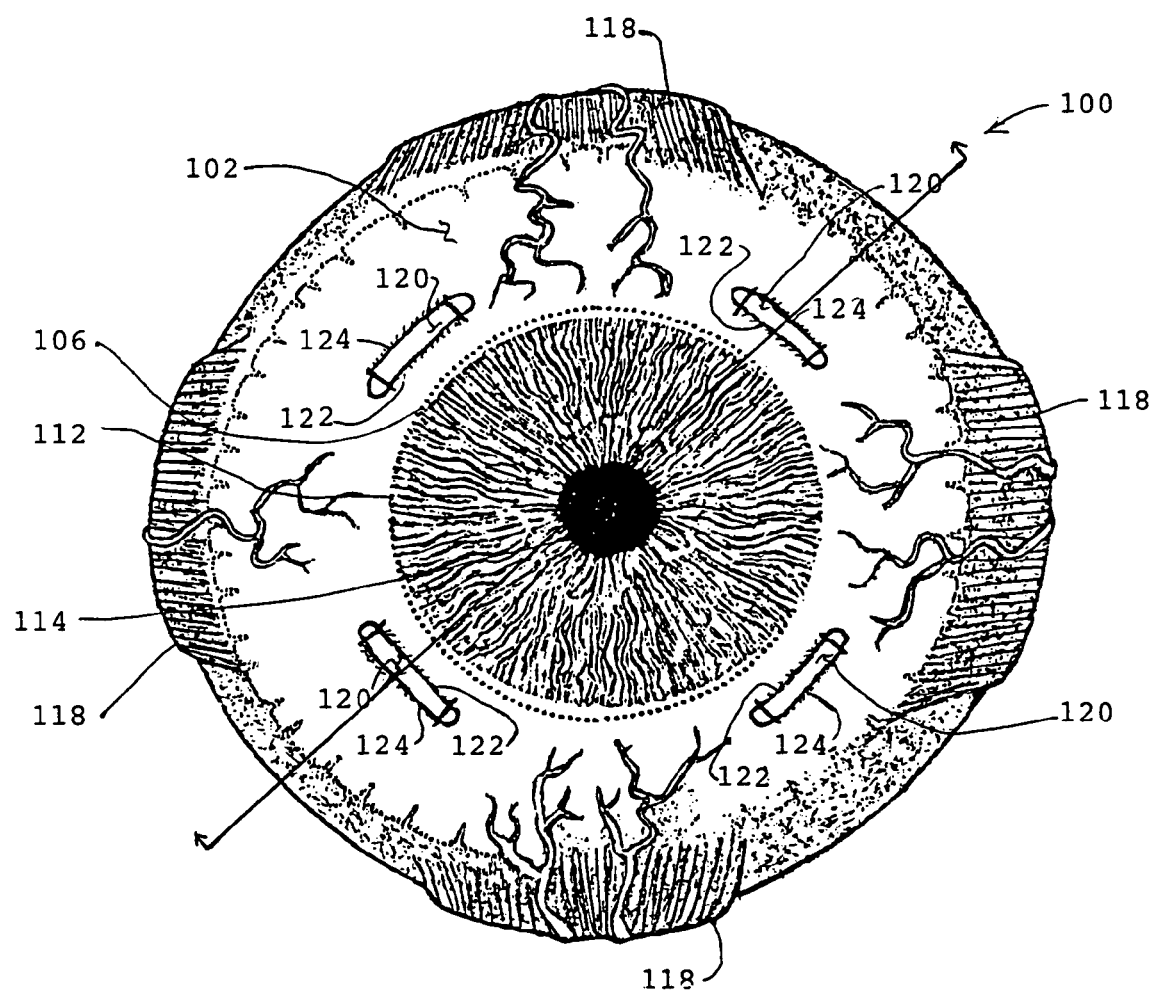
FIG. 28 shows a front elevational view of an eye having four prostheses of the type illustrated in FIGS. 24-27 implanted in the sclera thereof.
Figure 29:
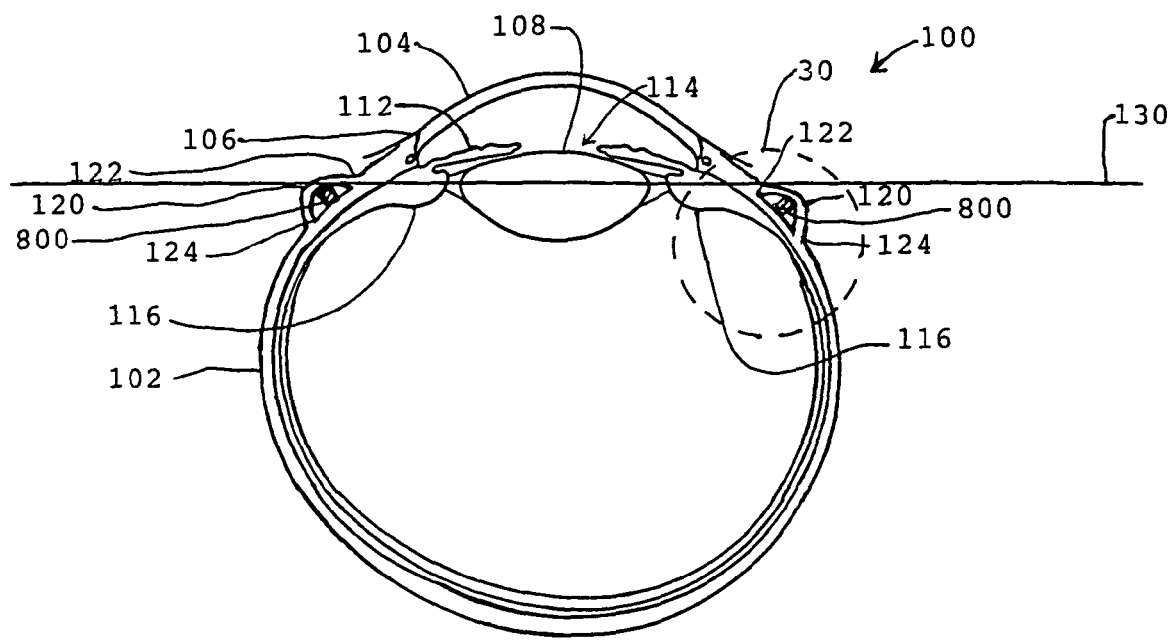
FIG. 29 shows a cross section of the eye of FIG. 28 along the line 29-29.
Figure 30:
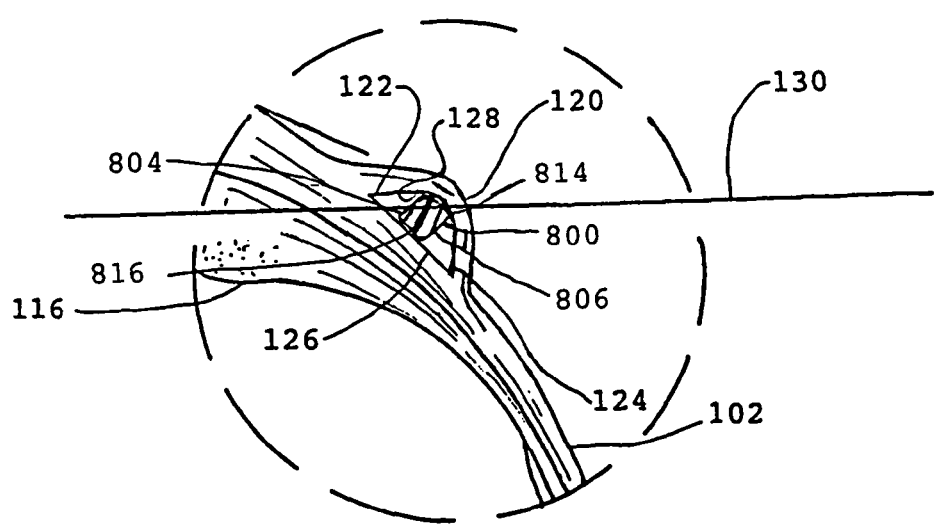
FIG. 30 shows an enlarged view of the cross section of FIG. 29 in the region indicated by the circle 30.

The position of the scleral prosthesis 800 when implanted in an eye is shown in the anterior elevational view of an eye, FIG. 28. FIG. 29 shows a cross-section of the eye shown in FIG. 28, along the line 29-29, showing the prostheses 800 in place in the scleral pockets 120. FIG. 30 shows an enlarged detail of the prosthesis 800 in the region defined by the circle 30 in FIG. 29.

Figure 2:
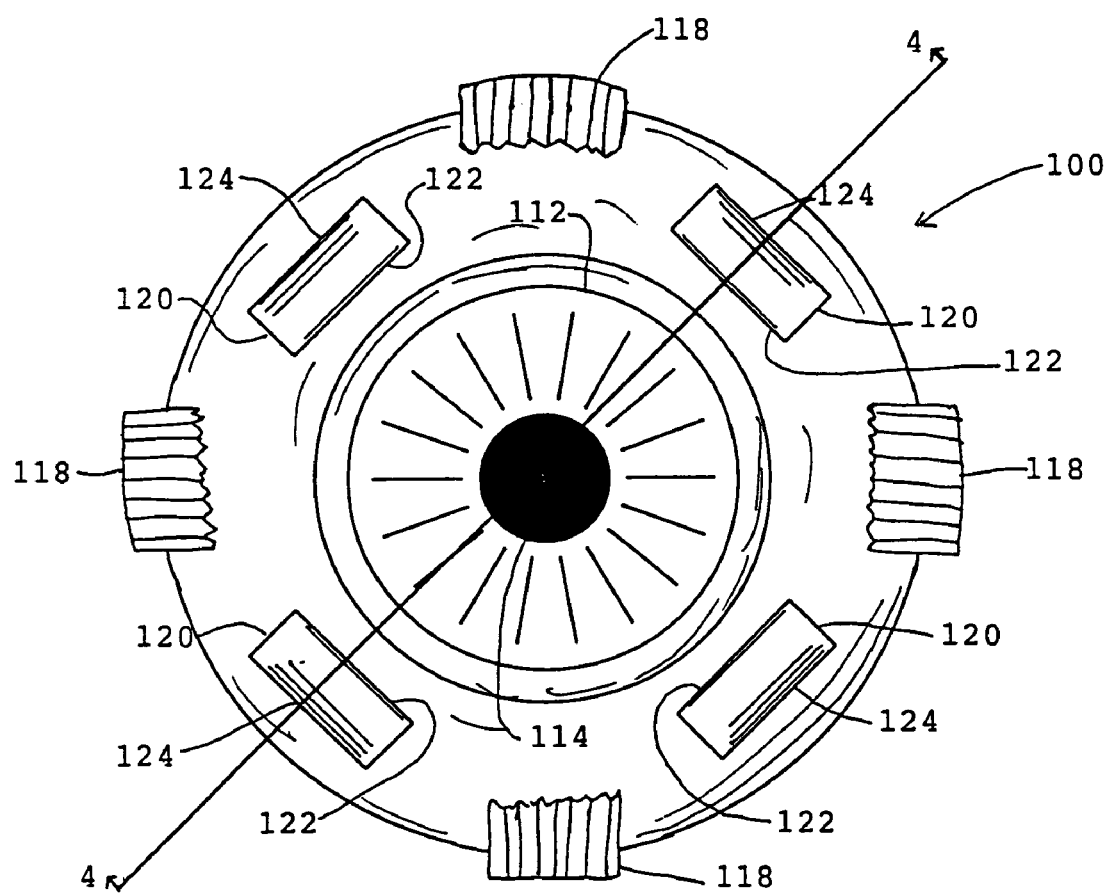
FIG. 2 shows a front elevational view of an eye showing the location of straight scleral pockets.

The height of the prosthesis between base surface 816 and ridge 814 is predetermined to elevate the flap of the scleral pocket or belt loop 120 sufficiently to exert an outwardly directed traction on at least the anterior margin 122 of the scleral pocket that is sufficient to elevate the sclera adjacent to the anterior margin 122 by an amount sufficient to accomplish the purpose of the invention, i.e., to increase the working distance of the ciliary muscle and thereby restore the amplitude of accommodation of the presbyopic eye. Typically, the distance between the major surface 816 and the second surface or ridge 814 will be in the range of from about 0.3 millimeters to about 0.9 millimeters, preferably from about 0.5 millimeters to about 0.7 millimeters, and most preferably about 0.6 millimeters. The antero-posterior dimension of the prosthesis 800, as measured between the surfaces 804 and 806 in the illustrated embodiment, may range from about 0.3 millimeters to about 0.9 millimeters, preferably from about 0.5 millimeters to about 0.7 millimeters, and most preferably about 0.6 millimeters. It will be understood by those skilled in the art that the distances between the surface 816 and ridge 814 and between anterior edge or surface 804 and posterior edge or surface 806 may be varied as appropriate to fit in a scleral pocket of defined dimensions. These dimensions are chosen to accomplish the purpose of the invention, i.e., to produce an elevation of the sclera and associated ciliary body as discussed above. Consequently the actual cross sectional shape of the prosthesis may vary form that shown in FIGS. 24-27. The length of the scleral prosthesis 800, which may be referred to as the transverse dimension as implanted in an eye, is chosen to provide an outward traction along a sufficient length of the circumference of the sclera of the eye in the zone encompassing the ciliary body to provide an effective amount of elevation of the sclera and attached ciliary body to accomplish the purpose of the invention. The length chosen will also depend on whether the surgeon prefers to implant the prosthesis entirely within the length of the scleral pocket 120, or have the ends of the prosthesis extend beyond the ends of the scleral pocket, as shown in FIG. 28. It is preferred to have the ends 808, 810 of the prosthesis 800 extend beyond the lateral ends of the scleral pockets or belt loops, as shown in FIG. 28. When the prosthesis 800 is so dimensioned and positioned, the ends 808, 810 bear on the intact sclera adjacent to the ends of the scleral belt loops to enhance the outward force exerted on the outer flap of the scleral pocket or belt loop 120. Typically the transverse dimension of the prosthesis will range from about 3.0 millimeters to about 8.0 millimeters, preferably from about 3.5 millimeters to about 6.0 millimeters, more preferably from about 4.0 millimeters to about 5.0 millimeters, and most preferably about 4.5 millimeters. It will be understood by the skilled practitioner that the dimensions of the prosthesis are adapted to the dimensions of the individual eye in which they are implanted, the dimensions being chosen to achieve an effective increase in the diameter of the sclera in the zone of the sclera adjacent to the ciliary body to produce an accompanying increase in the diameter of the ciliary body to provide an effective treatment for presbyopia and the other eye disorders discussed herein. As a consequence of the possible variations in the dimensions of the prosthesis in the inner-outer (or height) dimension, the antero-posterior dimension, and the length or transverse dimension, the exact shape of the prosthesis may vary significantly from that shown in FIGS. 24-27. The dimensions and exact shape of the prostheses are to be adapted to the eye in which they are to be implanted. Ordinarily a plurality, preferably four prostheses are implanted as shown in FIGS. 2, 3, and 28. However, more or fewer prostheses can be implanted. Ordinarily, all the prostheses implanted in one eye will be identical, but it is not excluded that prostheses of different shapes and dimensions may be implanted to achieve results desired by the surgeon.

The scleral prosthesis of the invention is made of a material that is sufficiently rigid to exert a force on the sclera sufficient to produce the radial expansion required by the method of the invention and that is physiologically acceptable for long-term implantation or contact with the ocular tissues. Such materials are well-known in the surgical art and include suitable metals, ceramics, and synthetic resins. Suitable metals include titanium, gold, platinum, stainless steel, tantalum and various surgically acceptable alloys, and the like. Suitable ceramics may include crystalline and vitreous materials such as porcelain, alumina, silica, silicon carbide, high-strength glasses and the like. Suitable synthetic materials include physiologically inert materials such as poly (methyl methacrylate), polyethylene, polypropylene, poly(tetrafluoroethylene), polycarbonate, silicone resins and the like. The prosthesis may also be made of composite materials incorporating a synthetic resin or other matrix reinforced with fibers of high strength material such as glass fibers, boron fibers or the like. Thus, the segment may be made of glass-fiber-reinforced epoxy resin, carbon fiber-reinforced epoxy resin, carbon fiber-reinforced carbon (carbon-carbon), or the like. The segment may be made of a semi-rigid exterior and a liquid or gel filled interior so that the internal and external dimensions can be altered by injecting various amounts of liquid: water, saline, or silicone oil; or various amounts of a gel: silicone, collagen, or gelatin. The semi-rigid exterior may be made of any of the already listed materials. It will also be understood by the skilled practitioner that the material of which the scleral prosthesis is made may be adapted to the particular shape or design chosen for the prosthesis. For example, a prosthesis such as that shown in FIGS. 17-20 may be made of a material that can deflect and stretch under the internal pressure of the liquid or the like with which it is filled, whereas a prosthesis of the type shown in FIGS. 24-28, which receives support from regions of the intact sclera adjacent to the ends of the scleral pockets or belt loops may preferably be made of a relatively rigid material. A preferred material for the entire segment is surgical grade poly(methyl methacrylate).

The scleral prosthesis of the invention may be manufactured by any conventional technique appropriate to the material used, such as machining, injection molding, heat molding, compression molding and the like.

The scleral prosthesis may be foldable to facilitate insertion into a scleral belt loop or made in a plurality of parts so that it can be assembled prior to use or may be installed separately to form a complete prosthesis.

In practicing the method of the invention, the surgeon locates the proper region of the sclera to be expanded by measuring a distance of preferably 2.0 millimeters posterior of the limbus. At 2.5 millimeters clockwise and counterclockwise from each of the 45° meridians of the eye, and 2 millimeters posterior to the limbus, partial scleral thickness radial incisions, i.e., antero-posterior incisions, are made which are 2 millimeters long and 350 microns deep. Using a lamella blade the sclera is dissected until the partial thickness incisions are connected so that four scleral pockets or belt loops are made which have an anterior length of 5 millimeters, and a length extending generally axially of the eye of 2 millimeters. Thus, each pocket or belt loop is preferably centered over the 45° meridian of the eye. A prosthesis is then inserted in each of the four scleral belt loops. This produces symmetrical scleral expansion which will produce the desired result of increasing the effective working distance of the ciliary muscle.

The location of the prostheses of the invention when implanted in the eye is illustrated in FIGS. 1-4. FIG. 1 is an isometric view of an eye 100 having a globe 102 with the relevant exterior anatomical parts indicated as discussed above.

FIGS. 2 and 3 show front elevational views of an eye 100 showing the scleral pockets 120 formed at approximately the 45° meridians of the eye, i.e., approximately halfway between the vertical and horizontal meridians of the globe. This location is preferred because it avoids interference with structures of the eye that are located generally on the vertical and horizontal meridians. FIG. 3 shows the use of curved scleral pockets 120 to permit the use of curved prostheses of the type illustrated in FIGS. 9 and 10. FIG. 2 shows the use of straight scleral pockets 120. Such straight pockets are somewhat simpler to prepare surgically: For many patients the use of straight prostheses can provide adequate treatment of their presbyopia.

FIG. 4 shows a cross-section of the eye, taken along the line 4-4 in FIG. 3, showing the placement of the prosthesis of the invention relative to the significant anatomical structures of the eye. This figure shows the general configuration of the scleral pockets 120 and the prostheses 200 of the type illustrated in FIGS. 6-8 in a preferred embodiment. The anterior margins 122 of the scleral pockets or belt loops 120 are located approximately in the plane 130 of the equator 110 of the lens 108. The ridge 210 of the prosthesis causes the anterior portion of the pocket to be expanded somewhat more than the posterior portion. This places the sclera at the anterior margin of the pocket under a radial tension and causes it to expand somewhat from its normal diameter at that position. This scleral expansion draws with it the underlying ciliary body 116 and causes the ciliary body to be drawn away from the equator 110 of the lens 108. Accordingly, the expansion of the ciliary body 116 operates to increase the working distance of the ciliary muscle and restore, at least in part, the ability of the eye to accommodate for clear focusing on objects at different distances. FIG. 5 shows an enlarged portion of one of the scleral pockets 120 with adjacent anatomical structures. It shows the relation of the scleral pocket 120 to the underlying structures and its location just posterior to the equator of the lens 108 and overlying the ciliary body 116.

The method of the invention which increases the amplitude of accommodation may also be of benefit in treatment of hyperopia in certain patients. Some youthful hyperopes can achieve relatively normal vision by compensating for their hyperopia through the natural accommodative ability of the eye. However, as this ability declines with age, they find that it becomes more difficult to attain normal vision by this process, and they begin to experience headaches and other symptoms, even at an age somewhat less than usual for the onset of presbyopia. Evidently, increasing the amplitude of accommodation by the method of this invention would be useful in restoring the ability of these patients to compensate for their hyperopia.

The method of this invention also has utility in the treatment of primary open-angle glaucoma, which shows a correlation with age in certain individuals. It has been found that, in general, intraocular pressure (IOP) exhibits a linear increase with increasing age. (Armaly, M.F., On the distribution of applanation pressure I. Statistical features and the effect of age, sex, and family history of glaucoma, Archives of Ophthalmology, Vol. 73, pp. 11-18 (1965)). Among the general population is found a group of individuals who develop abnormally high intraocular pressures as a result of primary open angle glaucoma, a disease which is one of the most prevalent causes of blindness in the world. According to the theory of this invention, the linear increase in IOP with age is a direct result of the decrease in distance between the lens equator and the ciliary muscle and the resulting linear decrease in the effective pull of the ciliary muscle. Since the ciliary muscle inserts into the trabecular meshwork, the decrease in pull will decrease the size of the trabeculum and/or the drainage pores and result in a linear increase of intraocular pressure with age. In this view, the patients who develop primary open angle glaucoma may have a congenital predilection to narrower pores, protein deposition in the pores, and/or a smaller trabecular meshwork, so that when the ability of the ciliary muscle to exert force declines, after the age of 40 or thereabouts, they tend to develop excessively elevated IOP.

The method of the invention which increases the effective working distance of the ciliary muscle, and thereby increases the force that it can exert when it contracts, restores the level of force which the ciliary muscle exerts on the trabecular meshwork to a value characteristic of a more youthful eye. In this way it is expected that the tendency of an eye that is disposed to develop primary open angle glaucoma as it ages would be overcome and the onset of this disease would be prevented or at least postponed.

The invention having now been fully described, it should be understood that it may be embodied in other specific forms or variations without departing from its spirit or essential characteristics. Accordingly, the embodiments described above are to be considered in all respects as illustrative and not restrictive, the scope of the invention being indicated by the appended claims rather than the foregoing description, and all changes which come within the meaning and range of equivalency of the claims are intended to be embraced therein.

I claim:

1. An ocular scleral prosthesis comprising:
   an elongated body adapted to be implanted in an elongated pocket surgically formed within scleral tissue of an eye in a zone of a globe of the eye exterior to a ciliary body of the eye, the pocket having (i) a base comprised of inner layers of the scleral tissue, (ii) a flap formed from outer layers of the scleral tissue, (iii) an anterior margin and (iv) a posterior margin,
   wherein the elongated body is non-circular and has a first free end and a second free end,
   wherein the elongated body also has a first surface and a second surface opposite the first surface, the first surface and the second surface being adapted to respectively contact the base and the flap of the scleral pocket when the prosthesis is implanted,
   wherein one of the first and second surfaces is planar, and
   wherein the other of the first and second surfaces comprises a ridge or a crest separated from the planar surface by a distance sufficient to elevate the flap relative to the base and exert outwardly directed traction on at least the anterior margin of the pocket when the prosthesis is implanted in order to at least one of: increase a working distance of a ciliary muscle of the eye and increase an amplitude of accommodation of the eye.

2. The ocular scleral prosthesis set forth in claim 1 wherein:
   the elongated body comprises a planform having a longer first dimension and a shorter second dimension; and
   the elongated body is curved along the first dimension.

3. A prosthesis adapted for contact with a sclera of an eyeball, the prosthesis comprising:
   an elongated body having a first free end and a second free end, wherein the first free end is more distal from the second free end than from any other portion of the elongated body, and wherein the first and second free ends are adapted to be unattached to any other prosthesis when the prosthesis is implanted, the elongated body including a first surface and a second surface opposite the first surface, the first surface and the second surface each adapted to contact a portion of the sclera when the prosthesis is implanted; and
   means for expanding the contacted sclera, when the prosthesis is implanted, to increase an effective working distance of a ciliary muscle of the eyeball;
   wherein one of the first and second surfaces is planar, and the means for expanding comprise a ridge or a crest on the other of the first and second surfaces.

4. The prosthesis set forth in claim 3 wherein at least one of the first surface and the second surface is generally smooth and is adapted to contact ocular tissue within a pocket surgically formed within the sclera of the eyeball when the prosthesis is implanted.

5. The prosthesis set forth in claim 3 wherein the prosthesis is at least one of generally rectangular, curved, and elongated.

6. The prosthesis set forth in claim 3 wherein at least one of the first surface and the second surface comprises an anterior edge and a posterior edge, and the ridge or crest has a maximum height above the elongated body at one of: (i) a location intermediate between the anterior edge and the posterior edge, (ii) a location less than halfway from the anterior edge to the posterior edge, and (iii) a location at the anterior edge.

7. The prosthesis set forth in claim 3 wherein the elongated body comprises a planform having a longer first dimension and a shorter second dimension.

8. The prosthesis set forth in claim 7 wherein the ridge or crest extends along at least a portion of the first dimension.

9. The prosthesis set forth in claim 7 wherein the first dimension is about five (5) millimeters and the second dimension is about two (2) millimeters.

10. The prosthesis set forth in claim 7 wherein the elongated body is curved along the first dimension.

11. The prosthesis set forth in claim 3 wherein the prosthesis is made of at least one of a physiologically acceptable metal, a ceramic material, a synthetic resin, a reinforced composite material, and a flexible material.

12. The prosthesis set forth in claim 3 wherein the prosthesis is provided with an internal cavity.

13. The prosthesis set forth in claim 12 wherein the internal cavity is filled with at least one of a fluid and a gel.

14. The prosthesis set forth in claim 12 wherein the internal cavity is filled with at least one of water, a saline solution, an oil, silicone, collagen, and gelatin.

15. A prosthesis for surgical implantation into a pocket in a sclera of an eyeball, the prosthesis comprising an elongated body having a first free end and a second free end, both ends adapted to be free of contact with any other prosthesis when the prosthesis is implanted, wherein the elongated body has no portions that are spaced apart from each other further than the first and second free ends,
wherein the elongated body includes a first surface and a second surface, the first surface and the second surface being adapted to contact the sclera when the prosthesis is implanted, wherein one of the first and second surfaces is planar and the other of the first and second surfaces comprises a ridge or a crest separated from the planar surface so as to apply an outward force on the scleral pocket when the prosthesis is implanted to elevate an overlying portion of the sclera to increase an effective working distance of a ciliary muscle of the eyeball.

16. The prosthesis set forth in claim 15 wherein the elongated body is generally rectangular.

17. The prosthesis set forth in claim 15 wherein the elongated body is arched along a long dimension thereof.

18. The prosthesis set forth in claim 15, wherein at least one of the first surface and the second surface comprises an anterior edge and a posterior edge, and the ridge or crest has a maximum height located intermediate between the anterior edge and the posterior edge.

19. The prosthesis set forth in claim 15, wherein at least one of the first surface and the second surface comprises an anterior edge and a posterior edge, and the ridge or crest has a maximum height located between the anterior and posterior edges less than halfway from the anterior edge toward the posterior edge.

20. The prosthesis set forth in claim 15, wherein the elongated body has a planform having a first dimension longer than a second dimension, wherein at least one of the first surface and the second surface is adapted to contact the sclera along the second dimension when the prosthesis is implanted.

21. A scleral prosthesis comprising a body adapted for contact with a sclera of an eye in a region of a ciliary body when implanted, the body being non-circular and having a first free end, a second free end, and a ridge or a crest projecting above surrounding portions of the body, the ridge or crest located between first and second edges of the body and extending along at least a majority of a length of the body from the first free end to the second free end, the ridge or crest adapted to exert a force with respect to the contacted eye to expand the sclera in the region of the ciliary body when the prosthesis is implanted;
wherein the ridge or crest is configured, when the prosthesis is implanted, to at least one of: increase a working distance of a ciliary muscle of the eye and increase an amplitude of accommodation of the eye.

22. The scleral prosthesis set forth in claim 21 wherein the ridge or crest is configured to exert the force to increase the working distance of the ciliary muscle of the eye.

23. The scleral prosthesis set forth in claim 21 wherein the ridge or crest is configured to exert the force to increase the amplitude of accommodation of the eye.

24. The scleral prosthesis set forth in claim 21 wherein the body further has an outer surface that is adapted to contact ocular tissue within a pocket surgically formed within the sclera of the eye.

25. The scleral prosthesis set forth in claim 24 wherein the body further has a base adapted to contact scleral tissue between anterior and posterior margins of the pocket when the prosthesis is implanted within the pocket, the base adapted to contact the scleral tissue along a width of the base when the prosthesis is implanted.

26. The scleral prosthesis set forth in claim 21 wherein the prosthesis has a generally rectangular planform.

27. The scleral prosthesis set forth in claim 21 wherein the body further comprises a planform having a first dimension longer than a second dimension, a first surface and a second surface, and a height, the ridge or crest formed by or projecting from the first surface, the second surface adapted to contact sclera tissue across the planform when the prosthesis is implanted within a pocket surgically formed within the sclera of the eye.

28. The scleral prosthesis set forth in claim 27 wherein the second surface is planar.

29. The scleral prosthesis set forth in claim 27 wherein the body comprises the ridge, the ridge extending along at least a portion of the first dimension of the body and formed by an intersection of a first portion of the first surface that extends substantially along the height of the body with a second portion of the first surface that slopes across both the planform and the height.

30. The scleral prosthesis set forth in claim 27 wherein the first dimension is about five millimeters and the second dimension is about two millimeters.

31. The scleral prosthesis set forth in claim 27 wherein the second surface is curved along the first dimension.

32. The sclera prosthesis set forth in claim 27 wherein the ridge or crest extends along at least a portion of the first dimension of the body.

33. The scleral prosthesis set forth in claim 21 wherein the prosthesis is made of at least one of a physiologically acceptable metal, a ceramic material, a synthetic resin, a reinforced composite material and a flexible material.

34. The scleral prosthesis set forth in claim 21 wherein the prosthesis is provided with an internal cavity.

35. The scleral prosthesis set forth in claim 34 wherein the internal cavity is filled with at least one of a fluid and a gel.

36. The scleral prosthesis set forth in claim 34 wherein the internal cavity is filled with at least one of water, a saline solution, an oil, silicone, collagen, and gelatin.

37. A scleral prosthesis comprising a body adapted for contact with a sclera of an eye in a region of a ciliary body, the body being non-circular and having:

(i) a base member having an elongated planform with a major dimension, a minor dimension, an inner major surface and a planar outer major surface, the body being adapted to contact ocular tissue of the eye in the region of the ciliary body when the prosthesis is implanted, and
(ii) a ridge or crest member on the inner major surface of the base member and along the major dimension of the base member and spaced apart from edges of the base member, wherein the ridge or crest member is adapted, when the prosthesis is implanted in the eye, to apply a force to the contacted ocular tissue to thereby expand the sclera in the region of the ciliary body, wherein the ridge or crest member is adapted to apply the force to the contacted ocular tissue when the prosthesis is implanted at a location spaced apart from any other prosthesis; and wherein the ridge or crest member is configured, when the prosthesis is implanted, to at least one of: increase a working distance of a ciliary muscle of the eye and increase an amplitude of accommodation of the eye.

38. The sclera prosthesis set forth in claim 37 wherein the ridge or crest member is configured, when the prosthesis is implanted in the eye, to exert the force to increase the working distance of the ciliary muscle of the eye.

39. The scleral prosthesis set forth in claim 37 wherein the ridge or crest member is configured, when the prosthesis is implanted in the eye, to exert the force to increase the amplitude of accommodation of the eye.

40. The scleral prosthesis set forth in claim 37 wherein the outer major surface is adapted to contact the ocular tissue within a pocket surgically formed within the sclera of the eye.

41. The scleral prosthesis set forth in claim 37 wherein the prosthesis is generally rectangular.

42. The scleral prosthesis set forth in claim 37 wherein the base member has an anterior edge and a posterior edge, wherein the ridge or crest member is located spaced apart from the anterior edge.

43. The scleral prosthesis set forth in claim 37 wherein the major dimension is about five millimeters and the minor dimension is about two millimeters.

44. The scleral prosthesis set forth in claim 37 wherein the prosthesis is made of at least one of a physiologically acceptable metal, a ceramic material, a synthetic resin, a reinforced composite material and a flexible material.

45. The scleral prosthesis set forth in claim 37 wherein the prosthesis is provided with an internal cavity.

46. The scleral prosthesis set forth in claim 45 wherein the internal cavity is filled with at least one of a fluid and a gel.

47. The scleral prosthesis set forth in claim 45 wherein the internal cavity is filled with at least one of water, a saline solution, an oil, silicone, collagen, and gelatin.

48. The prosthesis set forth in claim 37 wherein the body is curved along the major dimension.

49. A prosthesis that contacts a sclera of an eyeball, the prosthesis comprising a non-circular body having a first free end and a second free end spaced apart from the first free end such that no portion of the body overlaps any other portion of the body, the body also having a planform that is adapted to expand the contacted sclera and that includes top and bottom surfaces, one of the top and bottom surfaces being planar and the other of the top and bottom surfaces comprising a ridge or a crest separated from the planar surface so as to increase an effective working distance of a ciliary muscle of the eyeball, wherein each of the first and second free ends lacks a mechanism for coupling to an end of another prosthesis.

50. The prosthesis set forth in claim 49 wherein the top surface is adapted to contact ocular tissue within a pocket surgically formed within the sclera of the eyeball.

51. The scleral prosthesis set forth in claim 50 wherein the top surface is circumferentially shaped and is adapted to exert an outward force on the scleral pocket to elevate a portion of the sclera attached thereto to increase the effective working distance of the ciliary muscle of the eyeball.

52. The prosthesis set forth in claim 50 wherein the body further comprises a means for stabilizing the prosthesis within the scleral pocket.

53. The prosthesis set forth in claim 52 wherein the stabilizing means includes the bottom surface that is adapted to contact ocular tissue within the scleral pocket.

54. The prosthesis set forth in claim 53 wherein an ocular tissue contact area of the bottom surface of the body is at least substantially equal to an ocular tissue contact area of the top surface of the body.

55. The prosthesis set forth in claim 52 wherein the stabilizing means includes at least one of the first end and the second end that is adapted to fix the body within the scleral pocket.

* * * * *